US011002717B2

(12) United States Patent
Elizarov et al.

(10) Patent No.: US 11,002,717 B2
(45) Date of Patent: May 11, 2021

(54) SYSTEMS AND METHODS FOR CHARACTERIZING RADIOACTIVE ANALYTES

(71) Applicant: TRACE-ABILITY, INC., Culver City, CA (US)

(72) Inventors: Arkadij M. Elizarov, Woodland Hills, CA (US); Artem Y. Lebedev, Santa Monica, CA (US)

(73) Assignee: Trace-Ability, Inc., Van Nuys, CA (US)

( * ) Notice: Subject to any disclaimer, the term of this patent is extended or adjusted under 35 U.S.C. 154(b) by 573 days.

(21) Appl. No.: 15/725,683

(22) Filed: Oct. 5, 2017

(65) Prior Publication Data
US 2018/0045692 A1 Feb. 15, 2018

Related U.S. Application Data

(63) Continuation-in-part of application No. 14/866,684, filed on Sep. 25, 2015, now Pat. No. 10,895,563, (Continued)

(51) Int. Cl.
*B01J 19/00* (2006.01)
*G01N 30/62* (2006.01)
(Continued)

(52) U.S. Cl.
CPC ............ *G01N 30/62* (2013.01); *B01L 3/0293* (2013.01); *B01L 3/50273* (2013.01);
(Continued)

(58) Field of Classification Search
CPC ........ B01J 19/004; B01J 19/08; B01J 19/081; B01J 2219/00927; C07B 59/00; C07B 59/002; C07B 59/005; C07B 2200/05
See application file for complete search history.

(56) References Cited

U.S. PATENT DOCUMENTS

| 4,871,674 A | 10/1989 | Matsui et al. |
| 5,310,657 A | 5/1994 | Berzofsky |

(Continued)

FOREIGN PATENT DOCUMENTS

| CN | 1036078 A | 10/1989 |
| CN | 1249816 A | 4/2000 |

(Continued)

OTHER PUBLICATIONS

PCT Search Report & Written Opinion dated Jan. 26, 2016 for PCT/US2015/052448 entitled Palette-Based Systems for Analyte Characterization filed on Sep. 25, 2015 (Applicant—Trace-ability, Inc.); 16 pages.

(Continued)

*Primary Examiner* — Jill A Warden
*Assistant Examiner* — Dwayne K Handy
(74) *Attorney, Agent, or Firm* — Harness, Dickey & Pierce, P.L.C.

(57) ABSTRACT

A device for automated characterization of radioactive analytes that provides an integrated system with liquid handling and plate reading components. The device can be further configured to include a chromatographic subsystem. Also provided is a method of using such a device, providing addition of a radioactive sample and a sequence of operations involving the abovementioned components of the system. The system is configured with radiation shielding in such a way that manipulations of radioactive samples do not interfere with concurrent radioactive measurements.

13 Claims, 1 Drawing Sheet

Related U.S. Application Data which is a continuation-in-part of application No. 14/191,293, filed on Feb. 26, 2014, now Pat. No. 10,309,947.

(60) Provisional application No. 62/404,696, filed on Oct. 5, 2016, provisional application No. 62/171,183, filed on Jun. 4, 2015, provisional application No. 62/056,529, filed on Sep. 27, 2014.

(51) Int. Cl.

| | | |
|---|---|---|
| *G01N 30/74* | (2006.01) | |
| *G01N 30/88* | (2006.01) | |
| *G01N 30/90* | (2006.01) | |
| *G21F 7/00* | (2006.01) | |
| *B01L 3/00* | (2006.01) | |
| *G21F 1/08* | (2006.01) | |
| *C12M 1/00* | (2006.01) | |
| *C12M 1/12* | (2006.01) | |
| *G01N 21/77* | (2006.01) | |
| *C12Q 1/02* | (2006.01) | |
| *G01N 25/00* | (2006.01) | |
| *B01L 3/02* | (2006.01) | |
| *G01N 30/00* | (2006.01) | |
| *G01N 33/00* | (2006.01) | |
| *G01N 21/75* | (2006.01) | |
| *G01N 33/15* | (2006.01) | |
| *G01N 30/16* | (2006.01) | |
| *G01N 35/10* | (2006.01) | |

(52) U.S. Cl.
CPC ....... *B01L 3/502715* (2013.01); *C12M 23/04* (2013.01); *C12M 29/00* (2013.01); *C12M 45/20* (2013.01); *C12M 47/10* (2013.01); *C12Q 1/02* (2013.01); *G01N 21/77* (2013.01); *G01N 25/00* (2013.01); *G01N 30/74* (2013.01); *G01N 30/88* (2013.01); *G01N 30/90* (2013.01); *G21F 1/085* (2013.01); *G21F 7/00* (2013.01); *B01L 2200/082* (2013.01); *B01L 2300/0829* (2013.01); *G01N 30/16* (2013.01); *G01N 33/15* (2013.01); *G01N 35/1097* (2013.01); *G01N 2021/752* (2013.01); *G01N 2030/77* (2013.01); *G01N 2030/8804* (2013.01); *G01N 2033/0093* (2013.01)

(56) References Cited

U.S. PATENT DOCUMENTS

| | | |
|---|---|---|
| 5,479,969 A * | 1/1996 | Hardie .................. B65B 3/003 |
| | | 141/103 |
| 7,329,538 B2 | 2/2008 | Wainwright et al. |
| 8,021,611 B2 | 9/2011 | Roach et al. |
| 8,980,184 B2 | 3/2015 | Mueller et al. |
| 2002/0142301 A1 | 10/2002 | Hovig et al. |
| 2004/0022696 A1 | 2/2004 | Zigler et al. |
| 2004/0086437 A1 | 5/2004 | Jackson |
| 2004/0126279 A1 | 7/2004 | Renzi |
| 2006/0245980 A1 | 11/2006 | Kiselev et al. |
| 2009/0087924 A1 | 4/2009 | Bynum et al. |
| 2010/0019157 A1 | 1/2010 | Furlan et al. |
| 2010/0145630 A1 | 6/2010 | Ball et al. |
| 2011/0070158 A1 | 3/2011 | Nutt et al. |
| 2011/0070458 A1 | 3/2011 | Chian et al. |
| 2012/0077429 A1 | 3/2012 | Wernimont et al. |
| 2016/0228876 A1* | 8/2016 | Chu .................. C12Q 1/6806 |
| 2018/0065103 A1* | 3/2018 | Schopf .................. B01J 19/24 |

FOREIGN PATENT DOCUMENTS

| | | |
|---|---|---|
| CN | 1846136 A | 10/2006 |
| CN | 2898829 Y | 5/2007 |
| CN | 101000344 A | 7/2007 |
| CN | 101013137 A | 8/2007 |
| CN | 201935917 U | 8/2011 |
| CN | 102576007 A | 7/2012 |
| CN | 202433374 U | 9/2012 |
| CN | 103344464 A | 10/2013 |
| EP | 1940543 A2 | 7/2008 |
| WO | 2000062931 A1 | 10/2000 |
| WO | 2009153163 | 12/2009 |

OTHER PUBLICATIONS

1st Office Action in related CNSN 2015800599311 dated Apr. 27, 2018.

European Search Report and Opinion in corresponding EPSN 15845167.4 dated Mar. 26, 2018.

SA/KR, International Search Report and Written Opinion for International Application No. PCT/US2015/052448, dated Jan. 26, 2016, 5 pages.

* cited by examiner

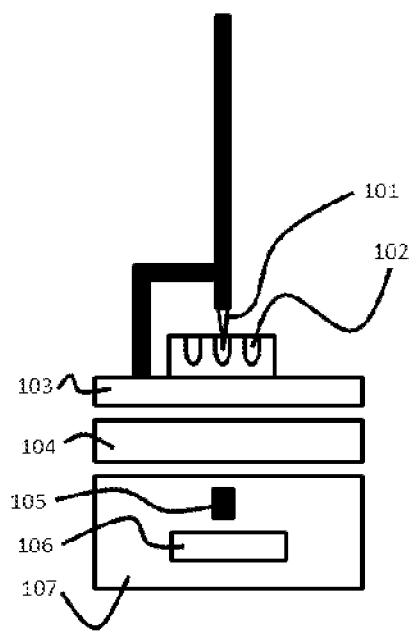
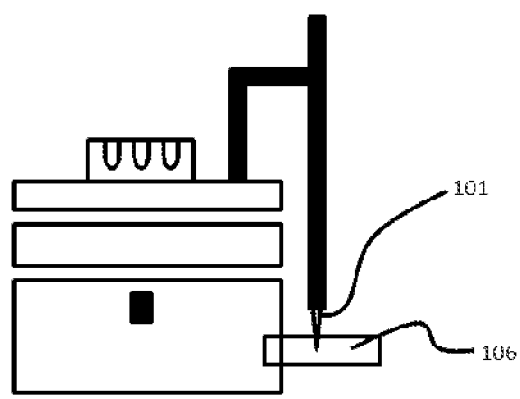
Figure 1a.  Figure 1b.
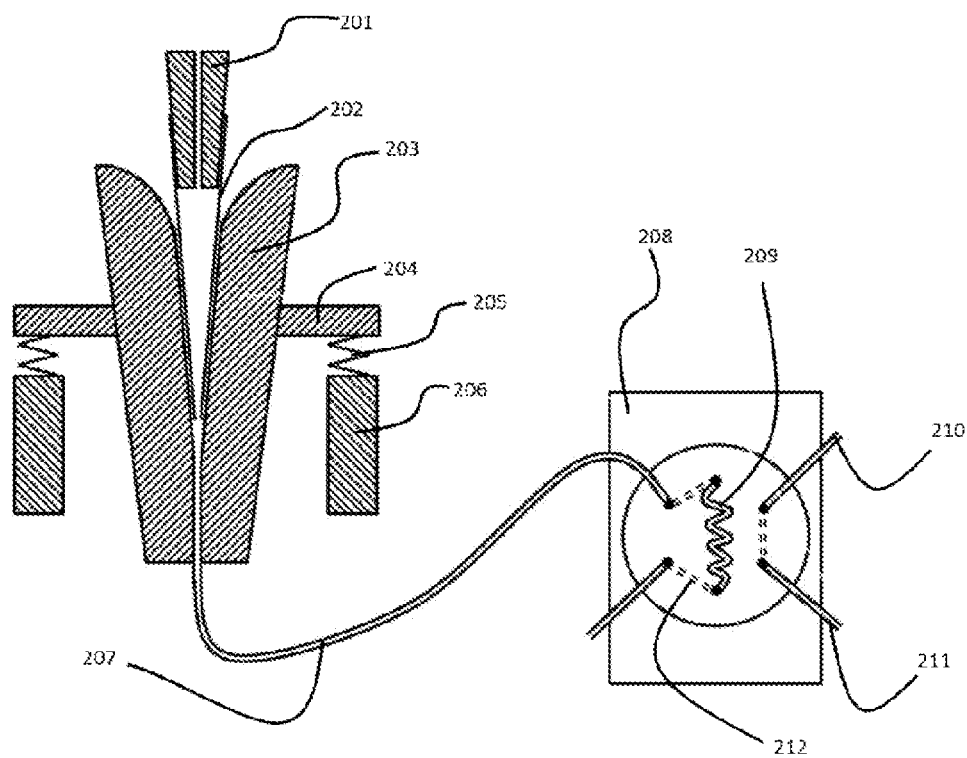
Figure 2.

SYSTEMS AND METHODS FOR CHARACTERIZING RADIOACTIVE ANALYTES

CROSS REFERENCE TO RELATED APPLICATION

This non-provisional application is a continuation in part of U.S. patent application Ser. No. 14/866,684, filed Sep. 25, 2015, and claims the benefit of U.S. Provisional Application No. 62/404,696, filed Oct. 5, 2016, the entire disclosure of which is hereby incorporated by reference in its entirety and for all purposes.

GOVERNMENT LICENSE RIGHTS

This invention was made with government support under R44CA192499 awarded by the National Institutes of Health and U01FD005517 awarded by the U.S. Food and Drug Administration. The government has certain rights in the invention.

FIELD OF THE INVENTION

The following description relates to systems and devices for chemical synthesis and/or analysis, and methods of using the same, in particular radiopharmaceuticals utilized in medical imaging such as Positron Emission Tomography (PET), or Single-Photon Emission Computed Tomography (SPECT); and/or therapy with such radioactive compounds.

BACKGROUND

The following description includes information that can be useful in understanding the inventive concept. It is not an admission that any of the information provided herein is prior art or relevant to the presently claimed invention, or that any publication specifically or implicitly referenced is prior art.

Utilization of radiopharmaceuticals (such as PET imaging agents) in clinical settings is limited by the short half-life of these reagents, which is typically measured in minutes or hours. Such short half-lives require on-site synthesis for any application of radiopharmaceuticals. However, clinical utilization further requires painstaking characterization of these reagents prior to administration to a patient. For example, each batch of radiopharmaceutical product has to be assessed for chemical identity, purity, radionuclide content, bacterial contamination, endotoxin content, and numerous other characteristics prior to administration.

In a typical radiopharmaceutical production facility, the tests used to characterize the radiopharmaceutical preparation are procedurally complex, requiring the use of highly trained personnel, and time consuming. In addition, safety precautions regarding the use of radioactive materials require the use of a workspace and equipment that is dedicated for this testing. Due to time constraints imposed by the short half-life of the radiopharmaceutical it is generally necessary to perform the necessary tests in a parallel fashion. A consequence of this is that a relatively large number of highly skilled personnel must be hired and trained, and significant laboratory space and equipment set aside, in order to support a radiopharmaceutical production. The expenses that this entails can be considerable.

Thus there remains a need for a system that simplifies, streamlines, and automates characterization of radiopharmaceuticals.

SUMMARY OF THE INVENTION

Brief Description of Figures

FIG. 1a schematically depicts a side view of an embodiment of the inventive concept, where the system is in the process of aspirating a sample. FIG. 1b schematically depicts a side view of an embodiment of the inventive concept, where the system is in the process of aspirating a sample.

FIG. 2 provides a cross section view of a system of the inventive concept, performing a step of fluid transfer for chromatographic analysis.

DETAILED DESCRIPTION

Recently, multi-parametric analysis systems have been reported that rely on optical analysis. The corresponding apparatus, systems and methods simplify and streamline characterization of radiopharmaceuticals in a clinical radiopharmaceutical production setting. Reagents for sample preparation and testing of radiopharmaceuticals are provided on a microwell plate or hybrid microwell/vial plate, along with one or more devices that facilitate separation of the components of chemical mixtures and real time monitoring of the separation. Results of all characterizing tests (including separation methods) are determined using an optical reader, such as a microplate reader.

Trace-Ability has been developing systems for multi-parametric analysis of radiopharmaceuticals. Such systems are enabled by palettes where sample interacts with reagents and features within the palette resulting in optical signals that can be detected outside the palette and correlated with specific sample parameters.

Palette-based systems for analyte characterization rely on a microplate reader as the single analysis device. Radioactive sample interacts with features and reagents in a palette which produces optical signals that can be detected and measured by the plate reader. Software then correlates these measurements with quantitative expression of sample characteristics (chemical, physical or radioactive). Since multiple parameters are being measured form a single palette, precise volumes of the sample and reagents need to be manipulated within the palette. Such manipulation requires precise pipetting. Although hand-held pipettes may suffice, their use would lead to personnel's radiation exposure and poor traceability of pipetting operations. Therefore, automated liquid handlers (pipettors) have been utilized to prepare the palette for assessment inside a plate reader.

Since typical imaging radiopharmaceuticals are short-lived, their analysis has to be completed rapidly. To achieve this, multiple operations need to take place simultaneously. Particular example of parallel operations is optical assessment of some sample parameters inside a plate reader while sample preparation for further analyses is being performed by the liquid handler. If the assessment being performed in this example is associated with radiation measurement, then radioactive sample manipulation in close proximity to the plate reader will likely interfere with such measurements. This problem has been observed multiple times during the system development.

All initial solutions had significant drawbacks. One example relied on spatial separation (in different rooms or separate radiation shielding enclosures) of the plate reader and liquid handler. Although the measurements were protected from the interfering radiation of materials manipulated simultaneously by the liquid handler, the user needed to move the palette back and forth between 2 locations. Such operation still has radiation exposure hazard for the staff and cannot operate in a fully-automated mode since it relies on a parson to carry the palette.

Other solutions that were envisioned relied on a wall of lead shielding between the liquid handler and the plate reader with an automated (robotic) mechanism for moving the palette back and forth. Although such solution would be fully automated, it required one more hardware component for transporting the palette and suffered from an increased footprint. The latter is important for 2 reasons. (1) Space is limited in typical radiopharmaceutical production facilities. (2) The whole system needs to be shielded (typically with lead), and the amount of lead required to shield a large system exceeds the weight limitation of a typical lab bench.

Finally, an inventive solution was found that solved the radioactive signal interference problem while actually dramatically reducing the overall system footprint. In an embodiment of this solution liquid handler is placed directly above the plate reader with a layer of shielding material between them. When the plate reader door is open and palette is exposed, the liquid handler can deliver samples and reagents located on its deck (above the shield) to the palette with an automated pipette. When the loaded palette is retracted into the plate reader for optical analysis, it ends up below the shield. Since Gamma rays travel only in straight lines, such arrangement eliminates all exposure by having the layer of shielding block all possible direct paths between the radioactive materials being handled by the liquid handler and the palette being analyzed by the plate reader. When the palette needs to be loaded, it protrudes out of the plate reader beyond the edge of the shield where it is accessible from above by the pipette of a liquid handler.

While still feasible, lateral arrangement (where liquid handler and plate reader are located on approximately the same level) is less desirable because the direct path needed for liquid transfer is horizontal and coincides with a horizontal path for gamma rays and other radiation. If one path is blocked by the shield, the other will be blocked too. In some embodiments lateral arrangement may be possible by having the pipette move around the shield. However vertical arrangement minimizes the amount of shielding needed and maximizes isolation of radioactive signals.

Another important advantage of the described system is its footprint. Stacked system with liquid handler above the plate reader occupies less than half of the bench space compared to a "side-by-side" system. Therefore, the shielding needed to protect the personnel from the radiation within the system can be easily cut in half.

An embodiment of the system described herein is presented in FIGS. 1a and 1b. FIG. 1a shows the system in the reading mode, where the palette is exposed to the detector inside the plate reader while the latter is completely protected from the liquid handler by the radiation shield. The pipette (101) draws the analyte from the palette (102) located within the liquid handler component (103) on the upper deck of the instrument. A layer of radiation shielding (104) is placed between the upper deck and the lower deck that includes a radiation-sensitive detector (105) and a second palette (106) which can be analyzed by that detector within the plate reader instrument (107) on the lower deck. FIG. 1b shows the system in the loading mode, where the pipette delivers the radioactive sample to the palette outside of the shielded area. AS shown, the pipette (101) is in the process of dispensing the analyte into the second palette (106) that has been ejected out of the lower deck plate reader instrument beyond the coverage of the radiation shield.

There are multiple embodiments of the present invention including, but not limited to plate reader placed below, above or to the side of the liquid handler. In other embodiments the relative positioning may be partially above or partially below. In some embodiments the shielding may be removable. In other embodiments the shielding may be made of a single component while in other embodiments it may consist of multiple components. In some embodiments the system may be used for analysis of a radiopharmaceutical. In some embodiments it may be used for analysis of other radioactive samples. In some embodiments it may be used to assess non-radioactive properties of a radioactive sample. In some embodiments it may be used to assess non-radioactive properties of a non-radioactive sample where radioactive reagents are used on the deck of a liquid handler. In some embodiments the system may be used to assess non-radioactive properties of a non-radioactive sample.

The small footprint of this system makes it useful beyond radioactive environments. In some of such embodiments the system where the liquid handler is placed entirely above the plate reader may be used without any radiation shielding.

Additional embodiment of the present invention is a system that comprises a liquid handler coupled with a chromatographic system such as HPLC (High Performance Liquid Chromatography). An example of such an embodiment is shown in FIG. 2. FIG. 2 depicts an embodiment of the current invention whereby an automated pipettor nozzle (201) with a pipette tip (202) is used to deliver analyte for chromatographic analysis. The pipette tip (202) forms a surface seal with the port (203) without reliance on any annular or other shoulders that form a line seal. To create a strong seal, the pipettor pushes the pipette tip (202) beyond the point of contact with the port. As a result, the port (203) exerts a back pressure enabled by the port's extensions (204) that rest on springs (205) that are connected to rigidly mounted components of the assembly (206) on the liquid handle deck. A flexible (non-rigid) connector (207) forms a continuous flow path between the injection port (203) that is not rigidly mounted on the instrument and the injection valve (208) which is rigidly mounted on the instrument, within the instrument or at any location not connected to the instrument. Its precise location is irrelevant to the success of the injection. The sample delivered by the pipette tip (202) to the port (203) can flow into the injection loop (209) of the injection valve (208) when the valve is in the loading position. The mobile phase flowing into the valve from the pump through port (210) exits via port (211) towards the separation device. Once the analyte is loaded into the injection loop (209), the internal passages (212) of the injection valve that are used to connect the loop to the injection port are switched to their alternative position that places the loop within the flow path between the pump and the separation device.

Such sample injection is an important component because while some radiopharmaceuticals can be analyzed relying only on optical methods enabled by a plate reader, many others require HPLC for at least one of their release tests. A system with integrated HPLC is more universal compared to the one comprised only of liquid handler and plate reader. It enables completely automated sample analysis of a large variety of analytes without any manual steps required for HPLC processes (injections of samples and standards, sample preparation, data analysis). The coupling between the liquid handler and HPLC is enabled at the injection port. Typically HPLC systems receive analyte samples via a needle that is inserted into an injection port coupled to a loop valve. The sample is delivered via a syringe through the needle into the loop. Then the loop valve is switched from "load" to "inject" position and the loop is placed in-line with the flow of the mobile phase that delivers the sample onto a chromatographic column. The challenge this presents for coupling with a liquid handler is that the latter typically does not operate with needles. Instead it uses disposable pipette tips to carry liquid from one location to another. A pipette tip cannot perform the functions of a needle to enable HPLC injection because it is conical while the HPLC injection ports are cylindrical. Therefore, a custom injection port had to be developed. There are 2 inventive features to the customized injection port presented herein.

First, the inner surface of the injection port is designed to be conical to match the outer surface of the disposable pipette tip. Such match creates a large surface area seal that prevents sample from escaping during injection. This seal does not rely on an annular shoulder that forms a circular connection. Sealing with the entire surface eliminates dead volume and in turn, minimizes cross contamination between injections.

Secondly, the injection port and the loop valve are separated in space connected by flexible tubing. This enables two critical advantages: (a) the loop valve does not have to be placed on the deck of the liquid handler, where space is limited, especially in a compact radiopharmaceutical instrument like the one described here. (b) it allows the seal to be reversible.

The latter aspect needs further explanation. Liquid handler is a precise robot that can deliver and hold the pipette tip at any location within its deck at precise coordinates. This would have been enough for a needle injection where the seal occurs in a uniform cylinder around the entire surface of the needle and small variations in depth of the needle penetration do not affect the seal. However, with a pipette tip making a seal against a conical surface of the injection port, small differences in position of that tip can lead to a difference between a good seal, no seal, or destroyed components resulting from pushing pipette tip beyond the physical stopping point at the surface of the port. If the tip stops short of the injection port, there will be no seal. If the tip is pushed past the point where it meets the injection port, it will be pushed with a lot of force against a valve body, which will likely deform the tip and make it jammed in the port (not a reversible seal). The seal needs to be reversible because once the injection has been completed, the tip needs to be removed and disposed to allow the liquid handler to continue other operations. Elimination of a rigid coupling between the injection port and the injection loop valve addresses the above issue. No force ever gets exerted against the rigidly-mounted valve body. The force gets exerted against the port that is connected to the valve via flexible tubing. The port is mounted on soft hardware (such as springs in one of the embodiments) that presses it gently against the pipette tip. This hardware can be mounted anywhere within the liquid handler deck and is not connected to the valve body. (See FIG. 2)

In further embodiments the above system may also comprise a plate reader and/or radiation shielding.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the embodiments below, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device for performing an analysis of a sample, comprising:
    a radiation shield;
    a plate reader including a sensor for detecting and measuring optical signals, the sensor being positioned on a first side of the radiation shield;
    a first source of radiation positioned in a container on an opposite second side of the radiation shield as the sensor; and
    a liquid handler positioned on the second side of the radiation shield, the liquid handler operable to deliver a liquid from the container containing the first source of radiation via a pipette to a palette spaced apart therefrom to define a second source of radiation, wherein the palette including the second source of radiation is moveable from a first position that is accessible by a tip of the pipette to a second position in optical communication with the sensor.

2. The device of claim 1, wherein the radiation shield is interposed between the sensor and a deck of the liquid handler.

3. The device of claim 2, wherein at least a portion of the radiation shield is positioned within a portion of one of the liquid handler and the plate reader.

4. The device of claim 1, wherein the liquid handler includes a disposable pipette and is operable to position the disposable pipette in communication with the liquid located on the second side of the radiation shield.

5. The device of claim 1, wherein the liquid handler is operable to deliver the liquid to locations within the plate reader.

6. The device of claim 1, wherein the plate reader includes a palette transfer mechanism for moving the palette to a position outside of a radiation shielded area within the plate reader.

7. The device of claim 1, further comprising a chromatographic device positioned to receive analyte automatically via the liquid handler.

8. The device of claim 7, wherein the chromatographic device includes a port having a shape complementary to a shape of the pipette tip of the liquid handler, the pipette tip sealingly engaging the port when liquid is being transferred to the chromatographic device.

9. The device of claim 8, wherein the chromatographic device includes a HPLC loop valve spaced apart from the port, the HPLC valve and the port being fluidly connected by a flexible tube.

10. The device of claim 1, wherein the liquid includes a radio-pharmaceutical.

11. The device of claim 8, wherein the injection port is coupled with a force-exerting device positioned to exert force opposite to a force exerted by the liquid handler via the disposable tip to create a seal between the disposable tip and the injection port.

12. The device of claim 11, wherein the force-exerting device comprises a spring.

13. The device of claim 11, wherein the force-exerting device is positioned such that force being exerted on the injection port is not exerted on a valve that directs analyte into a chromatographic flow stream.

* * * * *